(12) United States Patent
Schomacker et al.

(10) Patent No.: US 11,730,538 B2
(45) Date of Patent: Aug. 22, 2023

(54) PIGMENT TREATMENT SYSTEM AND METHODS OF USE THEREOF

(71) Applicant: Candela Corporation, Wayland, MA (US)

(72) Inventors: Kevin Schomacker, Maynard, MA (US); Xiaoming Shang, Lexington, MA (US)

(73) Assignee: CANDELA CORPORATION, Marlborough, MA (US)

(*) Notice: Subject to any disclaimer, the term of this patent is extended or adjusted under 35 U.S.C. 154(b) by 805 days.

(21) Appl. No.: 16/399,139

(22) Filed: Apr. 30, 2019

(65) Prior Publication Data

US 2020/0345417 A1 Nov. 5, 2020

(51) Int. Cl.
*A61B 18/20* (2006.01)
*A61B 18/00* (2006.01)

(52) U.S. Cl.
CPC .. *A61B 18/203* (2013.01); *A61B 2018/00452* (2013.01)

(58) Field of Classification Search
CPC ............ A61B 2018/00452; A61B 18/203
See application file for complete search history.

(56) References Cited

U.S. PATENT DOCUMENTS

| | | | |
|---|---|---|---|
| 5,749,868 A * | 5/1998 | Furumoto | A61B 18/22 606/9 |
| 6,613,042 B1 | 9/2003 | Tankovich et al. | |
| 2003/0149427 A1 | 8/2003 | Warner et al. | |
| 2008/0082089 A1 * | 4/2008 | Jones | A61N 5/0616 606/9 |
| 2014/0243804 A1 * | 8/2014 | Lukac | A61B 18/203 606/9 |
| 2014/0341239 A1 * | 11/2014 | Yoshino | H01S 3/2308 372/25 |
| 2014/0371730 A1 * | 12/2014 | Sierra | A61B 18/203 372/18 |
| 2017/0216619 A1 * | 8/2017 | Beerwerth | A61N 5/0617 |
| 2018/0074338 A1 * | 3/2018 | Shang | A61B 18/20 |
| 2020/0412082 A1 * | 12/2020 | Mirkov | H01S 3/1103 |

FOREIGN PATENT DOCUMENTS

| | | |
|---|---|---|
| WO | 199113652 A1 | 9/1991 |
| WO | 2004052181 A2 | 6/2004 |
| WO | 2005096783 A2 | 10/2005 |

OTHER PUBLICATIONS

International Search Report and Written Opinion regarding PCT/US2019/029953 dated Jan. 15, 2020, 16 pages.
Office Action dated Mar. 7, 2023 from related JP Application No. 2021-556372, 15 pages.

* cited by examiner

*Primary Examiner* — Lynsey C Eiseman
*Assistant Examiner* — Amanda L Steinberg
(74) *Attorney, Agent, or Firm* — Polsinelli PC

(57) ABSTRACT

A pigment treatment system includes a handheld apparatus to receive a sub-nanosecond laser beam with a wavelength of about 480 nm to about 550 nm and output a sub-nanosecond laser beam with a wavelength of about 700 nm to about 740 nm. The handheld apparatus includes a monolithic crystal with a first surface coating and a second surface coating to facilitate the change in wavelength of the laser beam through the crystal.

22 Claims, 8 Drawing Sheets

PIGMENT TREATMENT SYSTEM AND METHODS OF USE THEREOF

FIELD

The present disclosure relates generally to systems and methods to deliver sub-nanosecond laser pulses. In at least one example, the present disclosure relates to systems and methods to generate and deliver 700 nm to 740 nm sub-nanosecond laser pulses from a handheld device for optimized pigment treatment.

BACKGROUND

Commercially available lasers are currently used for treating pigmented skin. However, some of these lasers have significant limitations in terms of clinical applications. As presented herein, an optimal wavelength and systems have been identified to deliver sub-nanosecond laser pulses to achieve more effective and safer treatment of pigmented lesions on the skin.

BRIEF DESCRIPTION OF THE DRAWINGS

Implementations of the present technology will now be described, by way of example only, with reference to the attached figures, wherein.

DETAILED DESCRIPTION

Figure 1:
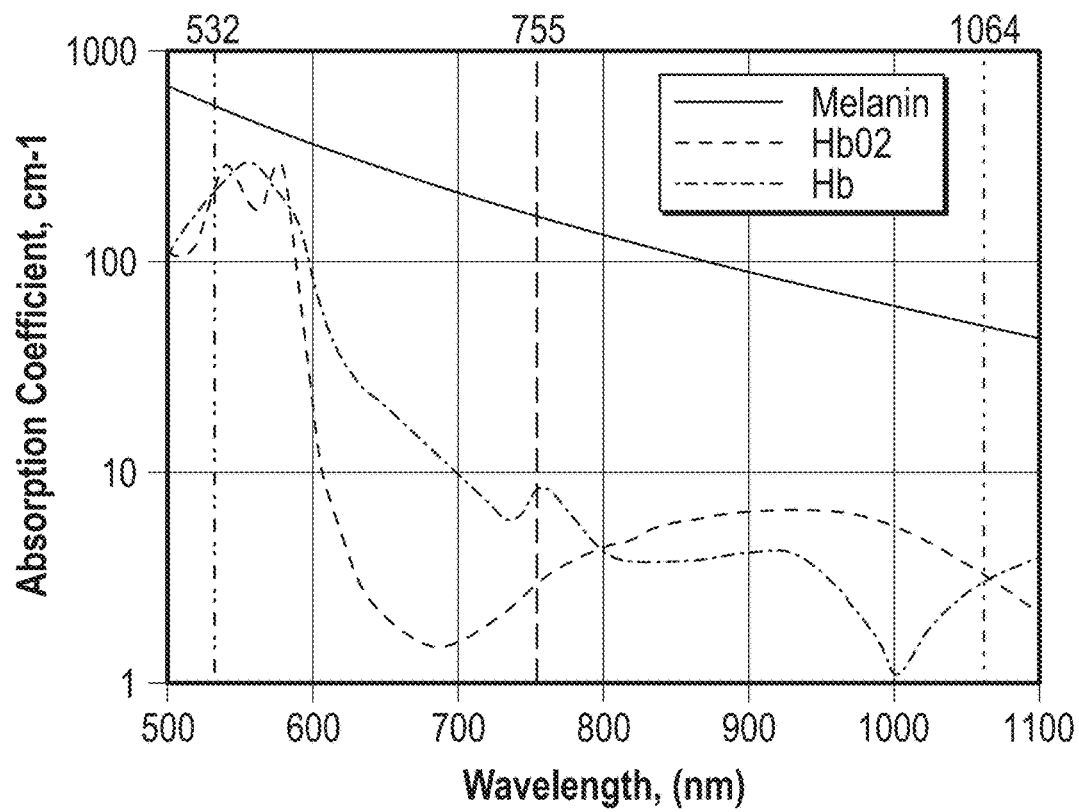
FIG. 1 is an absorption spectra of melanin and hemoglobin (including oxyhemoglobin and deoxyhemoglobin)

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, "substantially cylindrical" means that the object resembles a cylinder, but can have one or more deviations from a true cylinder. The terms "comprising," "including" and "having" are used interchangeably in this disclosure. The terms "comprising," "including" and "having" mean to include, but not necessarily be limited to the things so described.

Benign pigmented lesions have previously been treated with Q-switched nanosecond lasers. The use of nanosecond lasers for the treatment of pigmented lesions is based on the principle of selective photothermolysis of melanosomes. In general, the optimal pulse duration for selective photothermolysis is approximately equal to the thermal relaxation time (TRT) of the intended target structure. For lesions in which pigmented target cells are dispersed singly, such as nevus of Ota, the nanosecond pulse durations appear to be optimal. However, many adverse effects have been reported following the laser treatment. These include erythema, blistering, hypopigmentation and post-inflammatory hyperpigmentation. The risk of these complications is more common in Asian skin due to its higher epidermal melanin content. To mitigate these complications, a series of picosecond-domain lasers with pulse durations less than 1 ns may enable more efficient and faster removal of pigmented lesions with an improved safety margin.

At sub-nanosecond pulse widths, i.e. in the picosecond-domain, this efficacy is dramatically extended through defeating the stress relaxation time (SRT) of a target, allowing for even more effective pigment destruction with even less damage to the surrounding normal tissue. The mechanism of a picosecond laser interacting with melanosomes largely relies on photoacoustic (or photomechanical) effects as opposed to the combination of photothermal and photoacoustic effects for the nanosecond laser.

Although the tissue interaction mechanisms with a picosecond pulse and a nanosecond pulse are different, they all initiate from linear absorption of laser energy via targeted chromophore, i.e., melanin for pigmented treatment. For the skin in need of pigment treatment, there are two major competing chromophores resulting in absorption of laser energy, i.e., melanin and hemoglobin. Current commercially available sub-nanosecond lasers provide a set wavelength across a range (i.e., 532 nm, 670 nm, 755 nm, 1064 nm, etc.) that are intended for pigment treatment. Some of these wavelengths have significant limitations in terms of clinical applications. At the shorter wavelength, i.e., 532 nm, melanin absorption is so strong that the laser can penetrate only a very limited depth. This wavelength also causes higher risk of adverse effects for darker skin type. On the other hand, although the laser can penetrate deeper and be used for darker skin at longer wavelengths, i.e., 1064 nm, substantial absorption of hemoglobin can cause unwanted pin point bleeding or erythema. Provided herein is the determination of an optimal wavelength range to achieve a more effective and safer pigment treatment of pigmented lesions with minimal adverse effects. An apparatus for implementing such optimal treatment wavelength is also disclosed herein.

Figure 2:
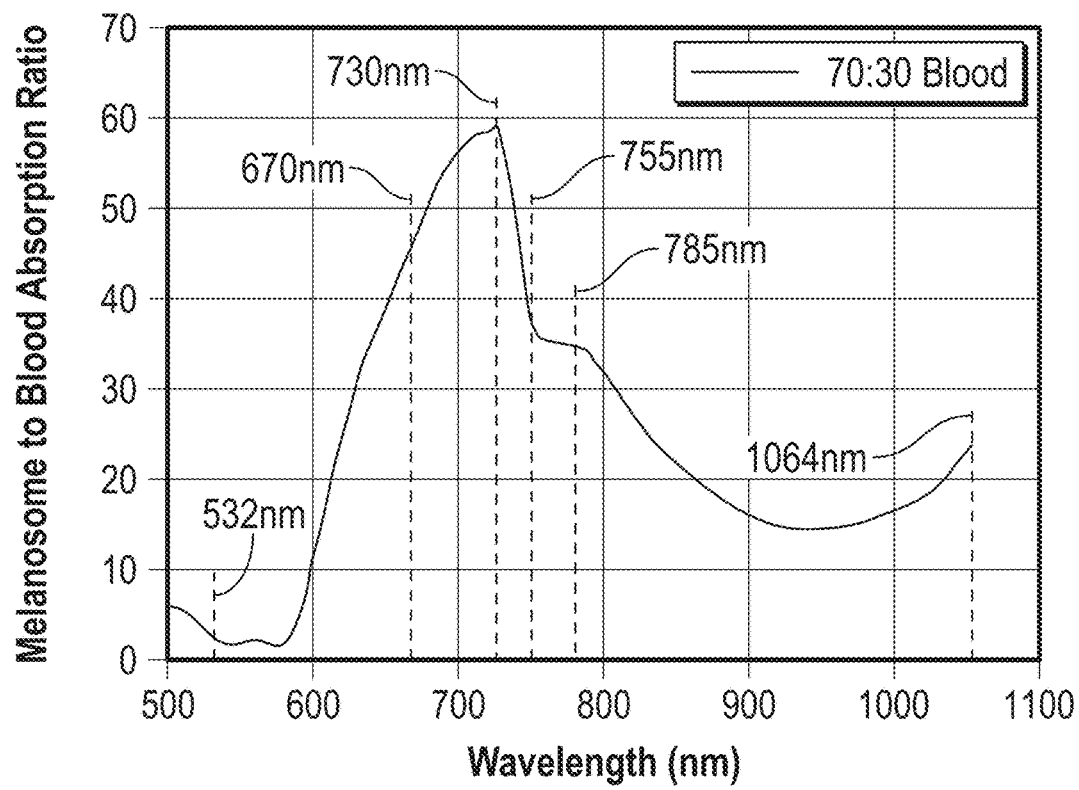
FIG. 2 is an absorption spectra of melanosome relative to hemoglobin.

To identify or determine an optimal wavelength range for pigmentation treatment, the relative absorption of melanin to hemoglobin was evaluated. As shown in FIG. 1, absorption coefficients for melanin and hemoglobin vary dramatically with the wavelength, and their variation trends are also different. More specifically, melanin exhibits monotonical decrease in absorption with the wavelength while absorption of hemoglobin (including oxyhemoglobin and deoxyhemoglobin) shows more features with several absorption bands. FIG. 2 represents the ratio of the melanin absorption to hemoglobin absorption. As shown in FIG. 2, the relative absorption of melanin is peaked at 730 nm. Therefore, at a wavelength of about 700 nm to about 740 nm, the melanin absorption is sufficient for pigmented treatment while adverse effects such as erythema and/or hemorrhage can be minimized. In some examples, a wavelength of about 730 nm is an optimal wavelength for effective and safer pigmented related treatment.

Figure 3:
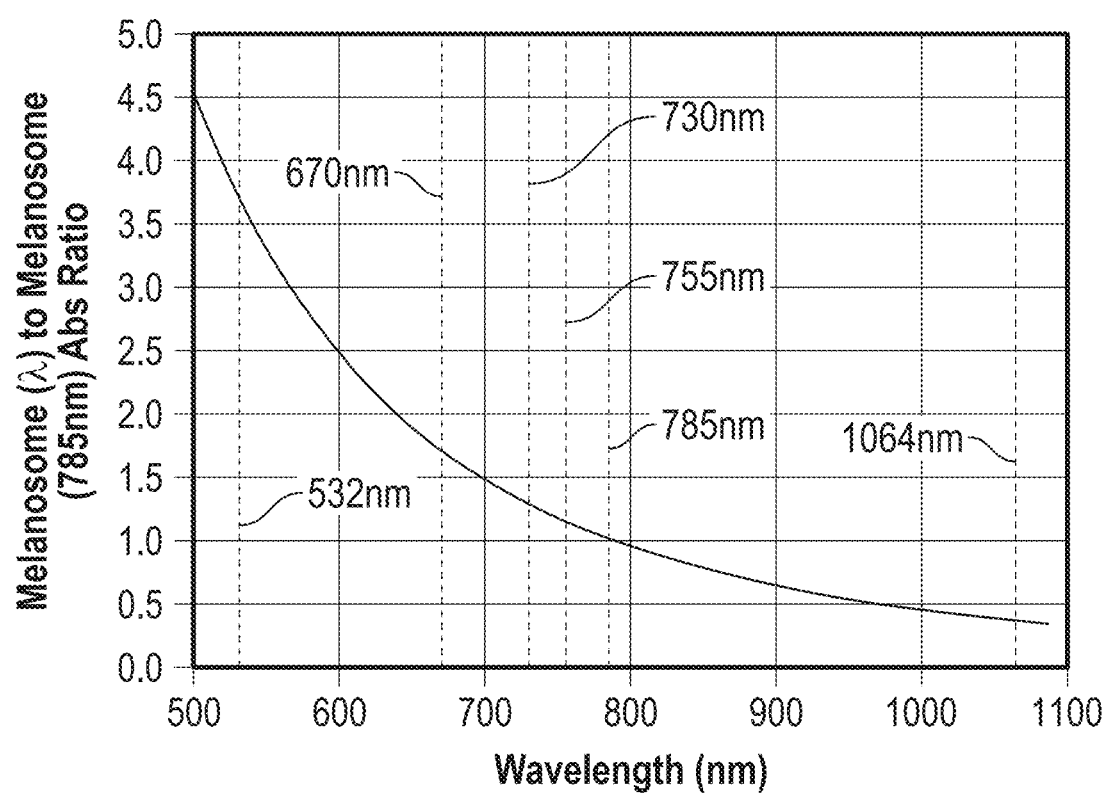
FIG. 3 is an absorption spectra of melanosome at various wavelengths relative to melanosome at 785 nm.

FIG. 3 represents the absorption ratio of melanosome to melanosome at 785 nm. The absorption of melanin is about 27% higher at 730 nm when compared to 785 nm so higher treatment efficiency may be expected at about 730 nm. In other words, the treatment fluence at 730 nm may be reduced by about 27% to deliver the same treatment effect as 785 nm. Alternatively, for the same fluence, photothermal and photoacoustic effects may be about 27% stronger. The treatment wavelength of about 700 nm to about 740 nm for pigmentation treatment provides for adequate absorption by melanin. In addition, the treatment wavelength of about 700 nm to about 740 nm provides for minimizing the absorption of the competing chromophores (mainly oxyhemoglobin and deoxyhemoglobin).

Disclosed herein is a handheld laser delivery apparatus to delivery sub-nanosecond pulsed laser beams at a treatment wavelength of about 700 nm to about 740 nm to a patient with a pigmented lesion for optimal treatment of the pigmented lesion while minimizing adverse effects. Non-limiting examples of pigmented lesions include dermal and epidermal pigment, commonly due to aging and photoaging such as lentigines, freckles, seborrheic keratosis and melasma, but can also include post-inflammatory hyperpigmentation, tattoos pigment, and pigment associated with wrinkles, scars, and acne scars.

Sub-nanosecond laser beams may be generated from a sub-nanosecond laser pumped optical parametric oscillator (OPO) or mode locked lasers (i.e., dye laser, Alexandrite, or Ti:Sapphire). However, the conversion efficiency of OPO may be compromised by unwanted energy loss due to presence of idler. Mode locking lasers usually involve long cavities and suffer from instability due to the high sensitivity to the environment perturbation and difficult manufacturability due to complex alignment. Furthermore, the pulse energy out of a mode locking cavity is on the order of a nanojoule. In order to obtain meaningful energy for skin treatment (i.e., >mJ), one has to employ complex amplification scheme, i.e., regenerative amplifier or/and multi-pass amplifiers.

Ti:Sapphire may be used to generate laser beams in the wavelength range between 700-900 nm via direct emission pumped in the visual wavelength region. However, the strongest emission of Ti:Sapphire is around 780 nm. So, in order to generate a shorter wavelength, a wavelength tuning element (e.g., birefringence filter) is typically inserted into the cavity to suppress the favorable emission at 780 nm. By doing so, cavity length can be increased significantly, and therefore it is hard to obtain short pulse.

The handheld laser delivery apparatus provided herein may utilize Ti:Sapphire for the favorable wavelength range but may be further modified such that sub-nanosecond pulses with meaningful energy for treatment can be generated.

Figure 4:
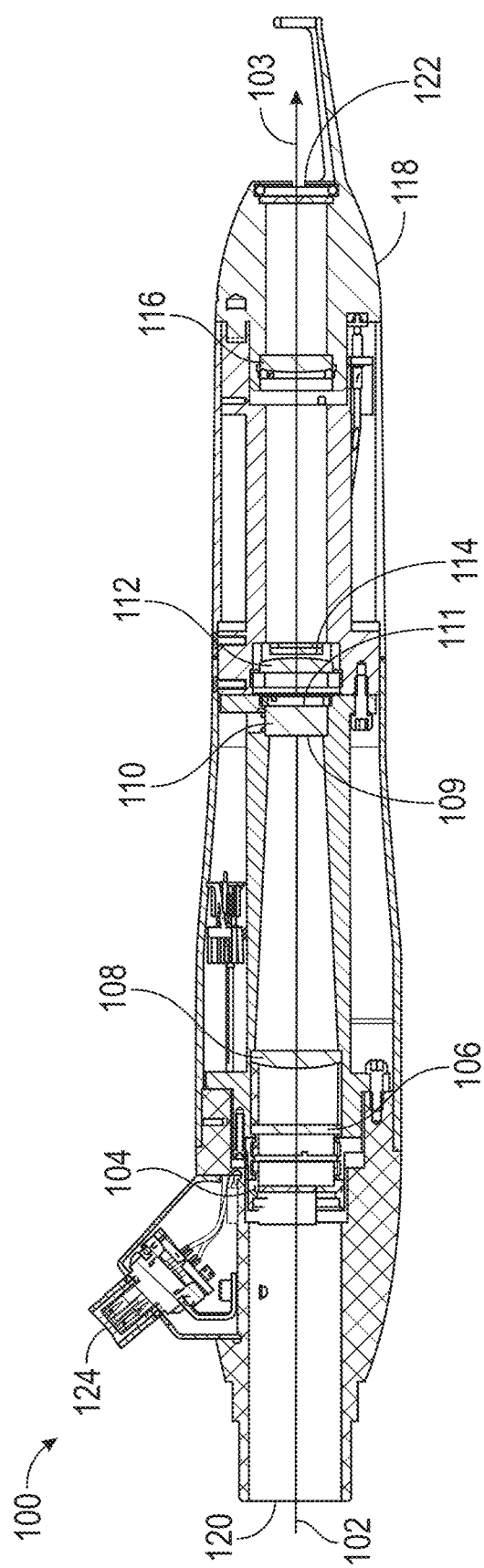
FIG. 4 is a diagram of a system to deliver 700-740 nm sub-nanosecond laser pulses according to the present disclosure.
Figure 5:
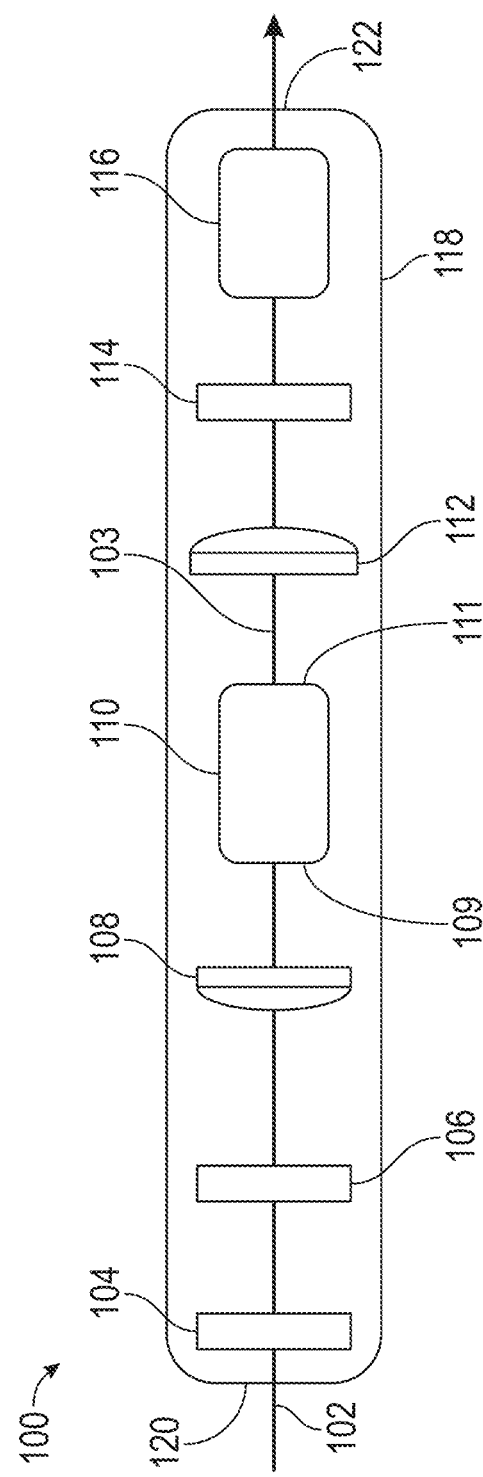
FIG. 5 is a diagram of a system to deliver 700-740 nm sub-nanosecond laser pulses according to the present disclosure.
Figure 6:
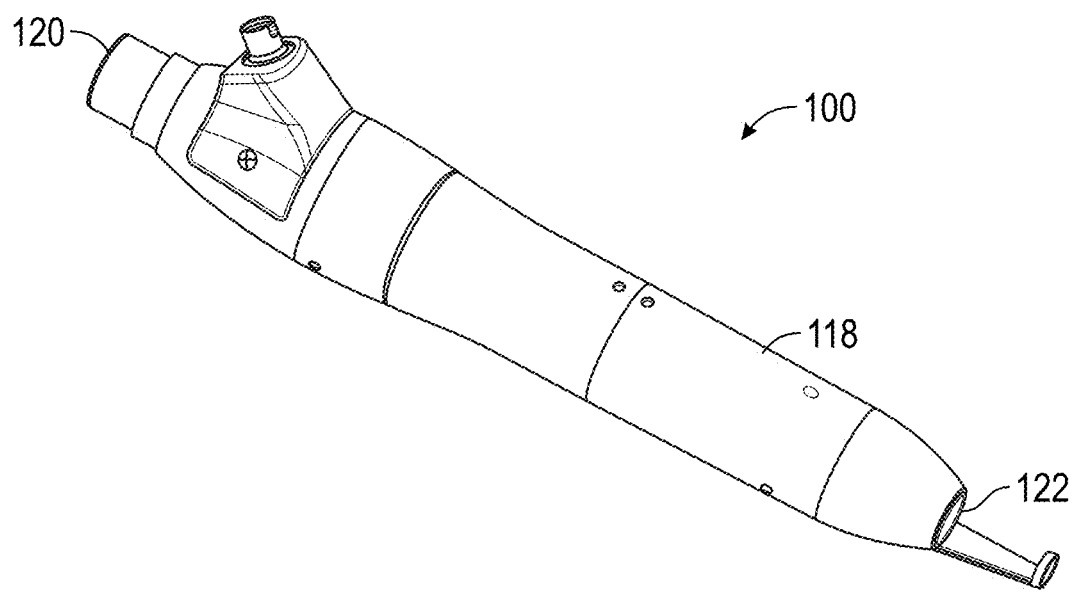
FIG. 6 is a diagram of a system to deliver 700-740 nm sub-nanosecond laser pulses according to the present disclosure.

FIGS. 4-6 illustrate the handheld laser delivery apparatus 100 for the treatment of skin pigmentation. In some examples, the handheld laser delivery apparatus 100 may be used to deliver sub-nanosecond laser pulses at a wavelength of 700 nm to 740 nm for the treatment and/or removal of pigmented lesions. The handheld laser delivery apparatus 100 includes a handheld body 118 having an inlet 120 operable to receive a sub-nanosecond pulsed laser beam having a first wavelength 102 and an outlet 122 operable output the sub-nanosecond pulsed laser beam at a second wavelength 103. In various examples, the first wavelength may be about 480 nm to about 550 nm and the second wavelength may be about 700 nm to about 740 nm. In some examples, the handheld body 118 may further include an electronic connector 124. In an example, the electronic connector 124 may be operable to allow console recognition of the handheld laser delivery apparatus with subsequent changes to the graphic user interface specific to the connected handpiece, among other features (e.g., spot size or beam pattern).

The handheld body may be of a reasonable size and weight that easily fits within a user's hand and is carriable with a hand. In at least one example, the handheld body may have a shape that facilitates it being held like a pencil. In other examples, the handheld body may include a pistol grip that facilitates the handheld body being held like a pistol.

Figure 7:
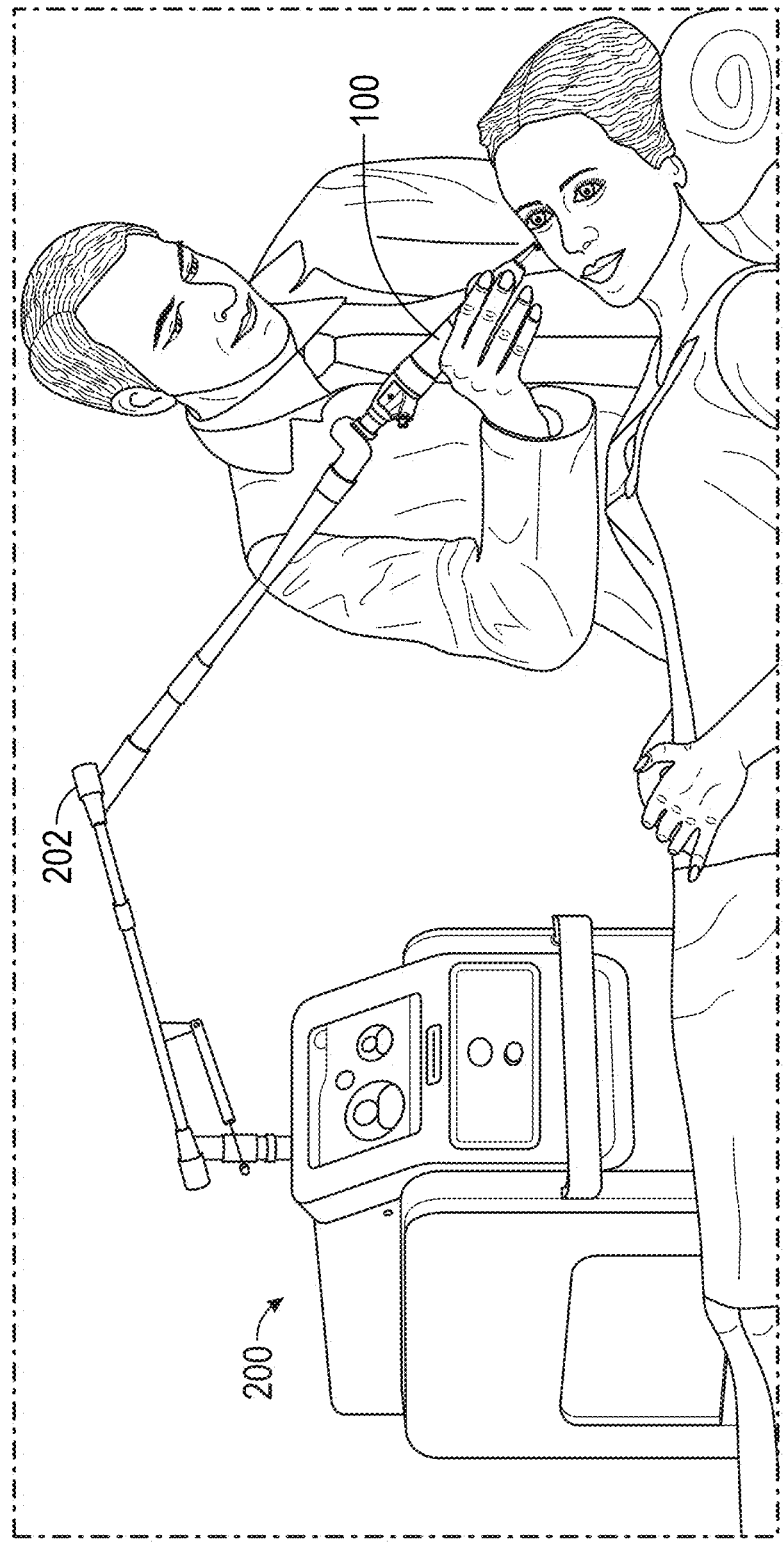
FIG. 7 is a diagram of a system to deliver 700-740 nm sub-nanosecond laser pulses according to the present disclosure.

Referring to FIG. 7, the inlet 120 of the handheld body 118 may be operably connected to a movable pump beam delivery system 200. For example, circularly polarized laser beams from a movable pump beam delivery system 200 may enter the inlet 120 of the handheld laser delivery apparatus. In an example, the movable pump beam delivery system 200 may include an articulated arm 202. In an example, the articulated arm may have a plurality of arms and a plurality of mirrors operable to direct the sub-nanosecond pulsed laser beam to a desired point on the handheld laser delivery apparatus by rotation around at least one rotary joint connecting the plurality of arms. In an example, the plurality of mirrors are operable to preserve incident laser beam polarization. In an example, the movable pump beam delivery system 200 may be operable to generate a circularly polarized laser beam having a wavelength of about 480 nm to about 550 nm. In at least one example, the movable pump beam delivery system 200 may be operable to generate a circularly polarized laser beam having a wavelength of about 532 nm.

Referring back to FIGS. 4 and 5, the handheld laser delivery apparatus 100 may further include a quarter waveplate 104 mounted onto a rotary stage within the handheld body 118 and operable to receive, from the handheld body inlet 120, the sub-nanosecond pulsed laser beam at the first wavelength 102. In at least one example, a circularly polarized laser beam may be converted into linearly polarized laser by the quarter waveplate 104 before it incidents on a homogenizer 106. The laser efficiency may be optimized by rotating the quarter waveplate 104 normal to the direction of the incoming pumped sub-nanosecond pulsed laser beam at the first wavelength 102. The orientation of the quarter waveplate 104 is locked down once the laser efficiency optimization is done. Referring to FIGS. 4 and 5, the handheld laser delivery apparatus 100 may further include a combination of a first homogenizer 106 and a focus lens 108 mounted within the handheld body 118. In an example, the combination is operable to receive the sub-nanosecond pulsed laser beam 102 from the quarter waveplate 104. The combination of the first homogenizer 106 and the focus lens 108 can provide a homogenized beam profile into a monolithic crystal 110 as a pump. In at least one example, the first homogenizer 106 and focus lens 108 may be operable to provide a homogenized pump beam profile and constant spot size in the Ti:Sapphire crystal to mitigate crystal damage and improve output energy stability.

As seen in FIGS. 4 and 5, the handheld laser delivery apparatus 100 may further include a monolithic crystal 110 mounted within the handheld body 118. The monolithic crystal 110 may form a laser resonator in the handheld body 118. The monolithic crystal 110 may convert the laser beam from a first wavelength 102 to a second wavelength 103. In an example, the monolithic crystal 110 is operable to receive the sub-nanosecond pulsed laser beam at the first wavelength 102 at a first end 109 of the monolithic crystal 110 and output the sub-nanosecond pulsed laser beam at the second wavelength 103 at a second end 111 of the monolithic crystal 110. In an example, the first end 109 of the monolithic crystal 110 may have a first surface coating and the second end 111 of the monolithic crystal 110 may have a second surface coating. For example, a laser resonator may be formed by the monolithic crystal 110 with a highly reflective first coating on its first end 109 and a partial reflective second coating on its second end 111.

In some examples, the laser beam 102 entering the monolithic crystal 110 may have a first wavelength of about 480 nm to about 550 nm and the laser beam 103 exiting the monolithic crystal 110 may have a wavelength of about 700 nm to about 740 nm. In an example, the laser beam entering the monolithic crystal 110 may have a wavelength of about 532 nm and the laser beam exiting the monolithic crystal 110 may have a wavelength of about 730 nm. The sub-nanosecond pulsed laser beam with the first wavelength may have a fluence that does not exceed 1.5 J/cm$^2$ to prevent coating damage. In some examples, the fluence of the laser beam entering the first end 109 of the monolithic crystal 110 may range from about 0.7 J/cm$^2$ to about 1.3 J/cm$^2$. In at least one example, the coating on the second surface may be highly reflective at the pump wavelength of 480 nm to 550 nm to implement double pass pumping. The wavelength selectivity is implemented by the second coating on the second end of the monolithic crystal 110. Therefore, there is no need to introduce additional wavelength tuning element in the cavity for selecting the operation wavelength. Such a monolithic design makes it possible to generate sub-nanosecond pulses at a fixed wavelength of 700 nm to 740 nm with a compact and alignment free design.

Figure 8:
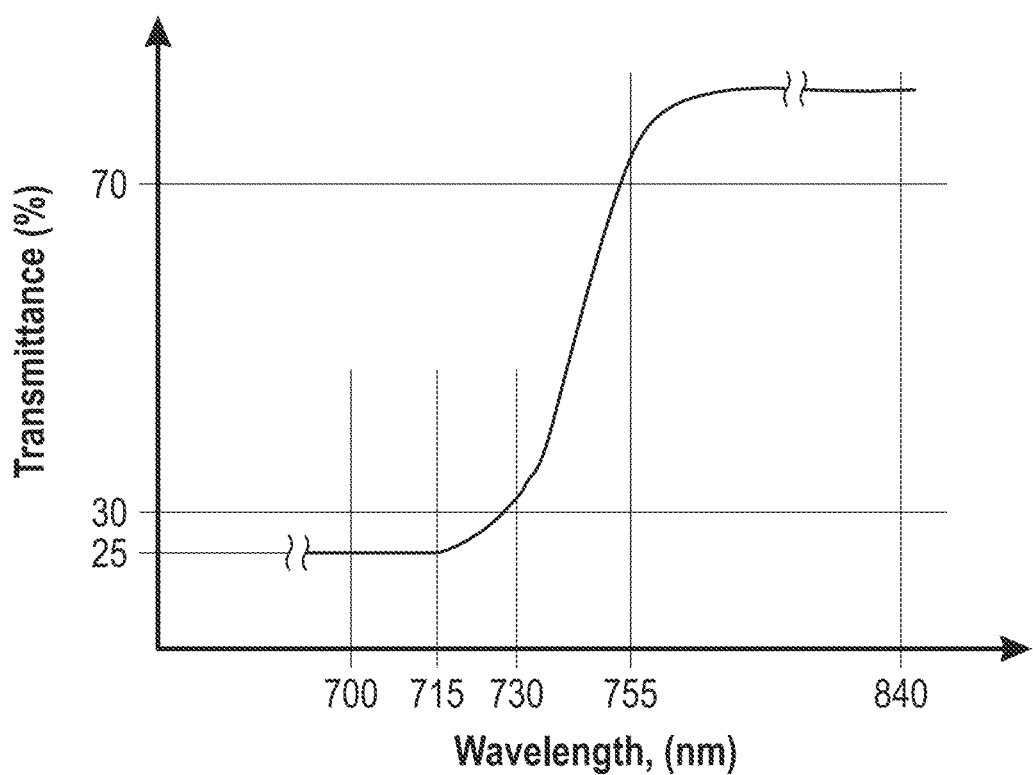
FIG. 8 is a graph of wavelength v. transmittance, showing the coating requirements for Ti:Sapphire rod surfaces.

In various examples, the monolithic crystal 110 may be Ti:Sapphire monolithic laser resonator. In an example, the Ti:Sapphire monolithic crystal may form a laser cavity by itself to generate the laser beam having the second wavelength 103. For example, the handheld laser delivery apparatus 100 may include a monolithic gain-switching Ti:Sapphire laser to generate an ultrashort laser pulse at a wavelength of about 700 nm to 740 nm. In some examples, the handheld laser delivery apparatus 100 includes a monolithic Ti:Sapphire crystal packaged into the handheld body 118 to generate 730 nm for pigment treatment. Instead of using a wavelength tuning element in the cavity, the wavelength selectivity may be implemented with high damage threshold optical surface coatings directly deposited on the Ti:Sapphire end surfaces with specific spectral requirements. For example, the surface coating on the first end 109 may be highly reflective at wavelengths from about 700 nm to 740 nm and highly transmissive at wavelengths of 480 nm to 550 nm. The surface coating on the second end 111 may be highly reflective at 480 nm to 550 nm for double pass pumping and highly transmissible at wavelengths from about 750 nm to about 850 nm for suppressing the favorable emission band of Ti:Sapphire laser. The same coating may also be partly reflective at 700 nm to 740 nm. Therefore, any wavelengths of 480 nm to 550 nm are reflected back into the crystal and only the desired wavelength of about 700 nm to 740 nm is transmitted out of the crystal. In some examples, the second end 111 coating may have a transmittance (T) of at least 75% at wavelengths from about 750 nm to about 850 nm. In other examples, the second end 111 coating may have a transmittance of about 30% at 730 nm which may monotonically increase by a slope of 2% per nanometer at wavelengths from about 730 nm to about 750 nm. In addition, FIG. 8 shows the parameters for the second end coating for the wavelength range from 700 nm to 843 nm, which stabilizes the laser operation at the desired 730 nm by eliminating the competing oscillation at a favorable emission at longer wavelengths, for examples at about 780 nm.

In some examples, the monolithic Ti:Sapphire crystal may be highly doped so that the linear absorption for a double pass pumping configuration may be greater than 90% in order to improve laser efficiency and avoid the damage of optics before the crystal by any unabsorbed pump laser. In other examples, the Ti:Sapphire monolithic crystal may have an internal absorption coefficient between about 3.8 cm$^{-1}$ and about 4.2 cm$^{-1}$ at the first wavelength so that the double pass absorption is greater than 90% while crystal doping may be distributed uniformly. Without being limited to any one theory, too high of doping may cause titanium ion aggregation leading to crystal damage risk and a non-uniform beam profile. In various examples, the laser beam exiting the Ti:Sapphire monolithic crystal may have a pulse duration of less than one nanosecond, less than 800 ps, less than 600 ps, less than 400 ps, less than 300 ps, less than 200 ps, or less than 100 ps. In an example, the Ti:Sapphire crystal may have a length of about 3 mm to about 5 mm to make it possible to generate sub-nanosecond laser pulses, typically around 300 ps at a pump fluence of 1.3 J/cm$^2$. In other examples, the Ti:Sapphire crystal may have a parallelism of the two end surfaces of up to about 5 arc seconds, up to about 4 arc seconds, up to about 3 arc seconds, up to about 2 arc seconds, and/or up to about 1 arc second. In at least one example, the two end surfaces of the Ti:Sapphire monolithic crystal may have a parallelism of less than or equal to 5 arc seconds.

Referring back to FIGS. 4 and 5, the generated laser beam at the second wavelength 103 out of the monolithic crystal cavity may be collimated with a collimating lens 112 mounted within the handheld body 118. The collimating lens 112 may be operable to receive the sub-nanosecond pulsed laser beam at the second wavelength 103 out of the monolithic crystal 110. Referring to FIGS. 4 and 5, the handheld laser delivery apparatus 100 may include a second homogenizer 114 mounted within the handheld body 118 and operable to receive the sub-nanosecond pulsed laser beam at the second wavelength 103 from the collimating lens 112. In an example, the Ti:Sapphire cavity may be collimated with a collimating lens 112 followed by a second homogenizer 114.

Again referring to FIGS. 4 and 5, the handheld laser delivery apparatus 100 may further include a beam delivery optical system 116 mounted within the handheld body 118. The beam delivery optical system 116 may be operable to receive the sub-nanosecond pulsed laser beam from the second homogenizer 114 and output the sub-nanosecond pulsed laser beam at the second wavelength 103 to the outlet 122 of the handheld body 118. For example, the laser beam propagating through the second homogenizer 114 may be delivered to the treatment site by the beam delivery optical system 116.

The use of the second homogenizer 114 in combination with the beam delivery optical system 116 produces a top hat (i.e. flat-top) beam profile for treatment. In at least one example, the second homogenizer 114 is followed by the beam optical delivery system 116 and provides a homogenized beam profile and stable spot size to be delivered to the treatment site. The delivered beam can be solid single beam of different sizes or a microbeam array. In an example, the output from the beam delivery optical system 116 may be a single beam and/or a plurality of fractionated microbeams. Treatment fluences of the second wavelength at the skin surface can range from 0.1 to 10 J/cm$^2$ for the full beam. For fractionated microbeams, where multiple beams split from the single full beam, treatment fluences can go as high as 50 J/cm$^2$.

Figure 9A:
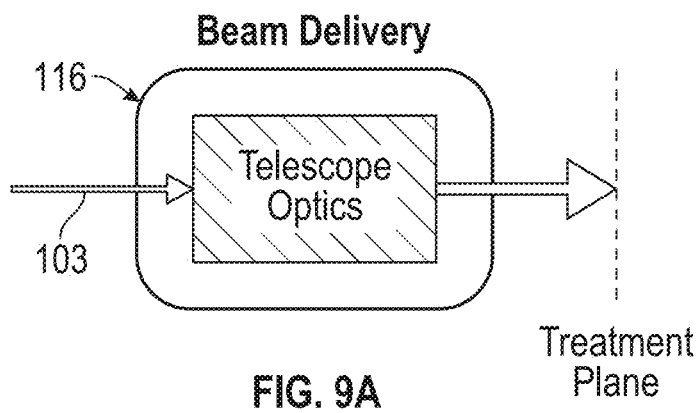
FIG. 9A is a diagram of a solid single beam delivery configuration.
Figure 9B:
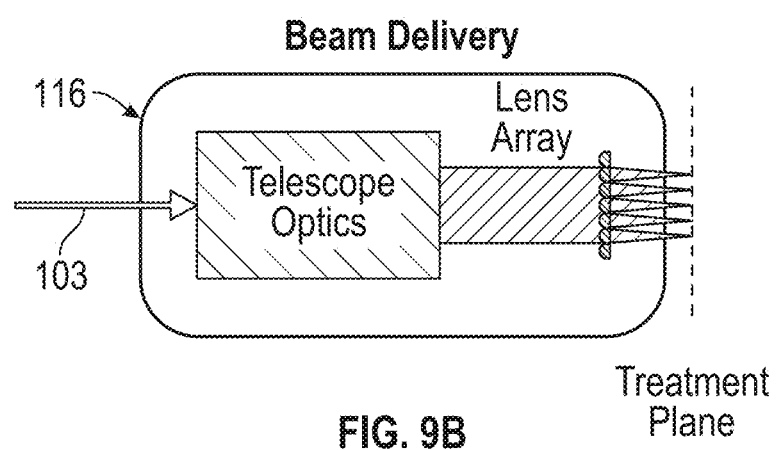
FIG. 9B is a diagram of a beam delivery configuration with a fractionated micro-beam pattern with a lens array.
Figure 9C:
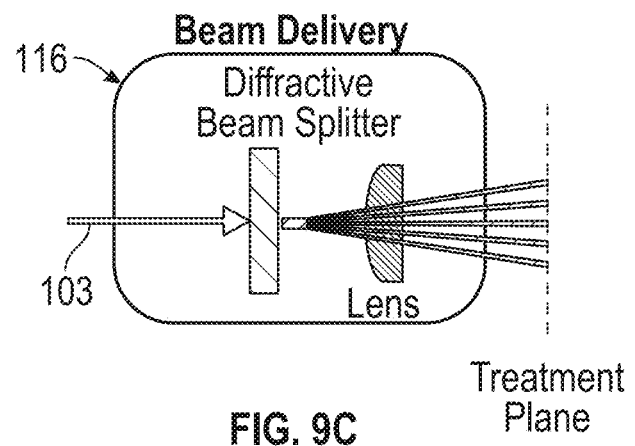
FIG. 9C is a diagram of a beam delivery configuration with a fractioned micro-beam pattern with a combination of diffractive beam splitter and a lens.

FIGS. 9A-9C show the three non-limiting examples of the beam delivery optical system 116 for generating different beam patterns. In an example, the beam delivery optical system 116 may include one of a telescope optics, a lens array, a diffractive beam splitter, and/or combinations thereof. More specifically, a solid single beam of a specific size may be generated with telescope optics (i.e., lens(es)), as seen in FIG. 9A. In an example, the treatment beam may have a size ranging from about 2 mm to about 10 min diameter. To deliver a fractionated microbeam array, a lens array (FIG. 9B) or a diffractive optic combining with a focusing lens (FIG. 9C) may be used. In an example, the fractionated microbeam array may include at least 25, at least 50, at least 75, and/or at least 100 evenly spaced, identical beams. For microbeams, spacing may be cubic or hexagonal packed, or any other arrangement of beams. The fractionated microbeams may be focused on to the skin surface or beneath the skin surface, or can be collimated onto the skin surface. In some examples, the fractionated microbeam sizes may range from as small as diffraction limited up to 0.2 mm in diameter.

Further provided herein is a laser delivery system including a pump beam delivery system 200 operable to deliver a sub-nanosecond pulsed laser beam having a wavelength of about 480 nm to about 550 nm and a handheld laser delivery apparatus 100. As seen in FIG. 7, the handheld laser delivery apparatus 100 may be attached to a movable pump beam delivery system 200 with an articulated arm 202, which may deliver sub-nanosecond laser pulses at about 480 nm to about 550 nm to the inlet 120 of the handheld apparatus for pumping the monolithic Ti:Sapphire laser. In an example, the sub-nanosecond laser pulses from the pump beam delivery system may be a green laser having a wavelength of about 532 nm. The pumping laser may be manipulated in such a way that its polarization is circularly polarized so that there is no polarization change when handheld apparatus is moved or rotated.

Further provided herein are methods of treating skin pigmentation. The method may include delivering a sub-nanosecond pulsed laser beam to a patient in need thereof using the handheld laser delivery apparatus 100. In an example the delivered pulsed laser beam may have a wavelength of about 700 nm to about 740 nm. In one example, the delivered pulsed laser beam has a wavelength of about 730 nm.

Figure 10:
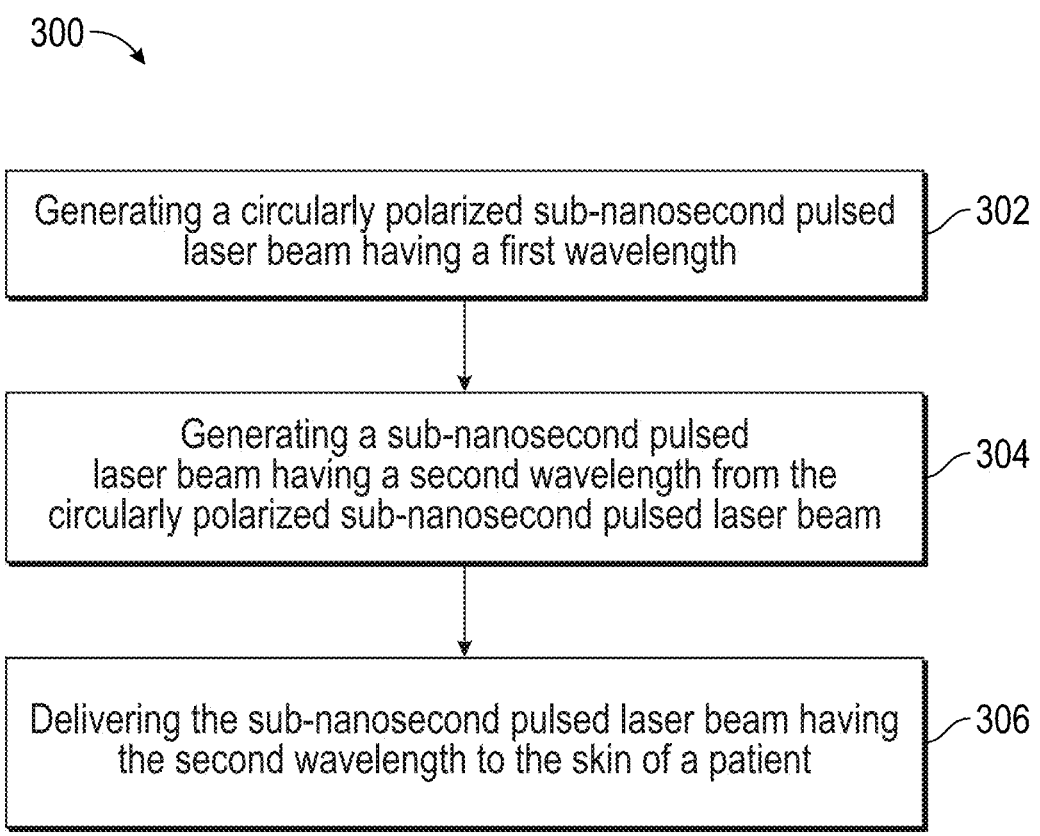
FIG. 10 is a flowchart of an exemplary method of treating a pigmented lesion by delivering sub-nanosecond laser pulses to a patient in need thereof.

Referring to FIG. 10, a flowchart is presented in accordance with an example embodiment. The method 300 is provided by way of example, as there are a variety of ways to carry out the method. The method 300 described below can be carried out using the configurations illustrated in FIGS. 1-2 and 8-9, for example, and various elements of these figures are referenced in explaining example method 300. Each block shown in FIG. 10 represents one or more processes, methods or subroutines, carried out in the example method 300. Furthermore, the illustrated order of blocks is illustrative only and the order of the blocks can change according to the present disclosure. Additional blocks may be added or fewer blocks may be utilized, without departing from this disclosure.

The example method 300 is a method of treating skin pigmentation in a patient in need thereof. In some examples, the skin pigmentation is a tattoo, wrinkle, and/or acne scar on the patient's skin to be removed or reduced. In at least one example, the tattoo is partially removed or fully removed. The example method 300 can begin at block 302. At block 302, a pump beam delivery system generates a circularly polarized sub-nanosecond pulsed laser beam at a first wavelength. In some examples, the first wavelength is about 480 nm to about 550 nm. In at least one example, the wavelength of the polarized sub-nanosecond pulsed laser beam is about 532 nm.

At block 304, a handheld laser delivery apparatus generates a sub-nanosecond pulsed laser beam from the circularly polarized sub-nanosecond pulsed laser beam. In an example, the generated sub-nanosecond pulsed laser beam is linearly polarized and has a second wavelength. In some examples, the second wavelength is about 700 nm to about 740 nm. In at least one example, the linearly polarized sub-nanosecond pulsed laser beam has a wavelength of about 730 nm.

At block 306, the sub-nanosecond pulsed laser beam having the second wavelength is delivered to the skin of the patient. The delivered beam targets melanosomes while minimizing damage to vessels and surrounding tissue of the patient. In an example, the delivered sub-nanosecond pulsed laser beam having the second wavelength is linearly polarized. In an example, the delivered laser beam has a wavelength of about 700 nm to about 740 nm. In at least one example, the delivered laser beam has a wavelength of about 730 nm. The delivered laser beam may provide optimal treatment of a pigmented lesion while minimizing adverse effects. Non-limiting examples of pigmented lesions include dermal and epidermal pigment, commonly due to aging and photoaging such as lentigines, freckles, seborrheic keratosis and melasma, but can also include post-inflammatory hyperpigmentation, tattoos pigment, and pigment associated with wrinkles, scars, and acne scars. For example, the delivered laser beam removes or reduces benign pigmented lesions, removes tattoos, and/or reduces pigment associated with acne scars, scars, and wrinkles.

The delivered laser beam may be applied to a target area of the patient's skin with the pigmented lesion. The target area may be on any area of the patient's skin, including but not limited to the face, arm, leg, back, chest, hand, or foot. In various examples, the delivered laser beam may be applied to the target area for up to about 15 to 20 minutes when treating a large area of diffuse pigment. Treatments may include the use of a full beam or a fractionated beam and may deliver up to about 5000 pulses, or more, depending on the size of the area treated. In at least one example, the delivered laser beam may be applied at a rate of about 5 pulses per second to about 10 pulses per second. Treatments can also include spot treatments (single pulses) of individual lesions such as lentigines or freckles which can be done relatively quickly, under one minute and typically done with the full beam and upwards of 100 pulses.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

Numerous examples are provided herein to enhance the understanding of the present disclosure. A specific set of statements are provided as follows.

Statement 1: A handheld laser delivery apparatus for treatment of skin pigmentation comprising a handheld body comprising an inlet operable to receive a sub-nanosecond pulsed laser beam having a first wavelength; and an outlet operable output the sub-nanosecond pulsed laser beam at a second wavelength; and a monolithic crystal mounted within the handheld body and operable to receive the sub-nanosecond pulsed laser beam at the first wavelength of about 480 nm to about 550 nm at a first end with a first surface coating and output the sub-nanosecond pulsed laser beam at the second wavelength of about 700 nm to about 740 nm at a second end with a second surface coating.

Statement 2: The handheld laser delivery apparatus of Statement 1, wherein the second wavelength is about 730 nm.

Statement 3: The handheld laser delivery apparatus of Statement 1, wherein the first wavelength is about 532 nm.

Statement 4: The handheld laser delivery apparatus of Statement 1, wherein the sub-nanosecond pulsed laser beam has a pulse duration of about 20 ps to about 750 ps.

Statement 5: The handheld laser delivery apparatus of any one of Statements 1-4, wherein the sub-nanosecond pulsed laser beam having the first wavelength received by the handheld body is circularly polarized.

Statement 6: The handheld laser delivery apparatus of Statement 1, further comprising a quarter waveplate mounted on a rotary stage within the handheld body and operable to receive, from the handheld body inlet, the sub-nanosecond pulsed laser beam at the first wavelength as a circularly polarized beam and output the sub-nanosecond pulsed laser beam as a linearly polarized beam; a combination of a first homogenizer and a focus lens mounted within the handheld body and operable to receive the sub-nanosecond pulsed laser beam from the quarter waveplate; a collimating lens mounted within the handheld body and operable to receive the sub-nanosecond pulsed laser beam at the second wavelength from the monolithic crystal; a second homogenizer mounted within the handheld body and operable to receive the sub-nanosecond pulsed laser beam from the collimating lens; and a beam delivery optical system mounted within the handheld body and operable to receive the sub-nanosecond pulsed laser beam from the second homogenizer and output the sub-nanosecond pulsed laser beam to the outlet of the handheld body.

Statement 7: The handheld laser delivery apparatus of any one of Statements 1-6, wherein the monolithic crystal is a Ti:Sapphire monolithic crystal.

Statement 8: The handheld laser delivery apparatus of Statement 7, wherein the Ti:Sapphire monolithic crystal is highly doped, has a linear absorption for a double pass pumping configuration of greater than 90%, and has an internal absorption coefficient between 3.8 $cm^{-1}$ and 4.2 $cm^{-1}$ at the first wavelength.

Statement 9: The handheld laser delivery apparatus of any one of Statements 1-8, wherein the monolithic crystal has a length of about 3 mm to about 5 mm.

Statement 10: The handheld laser delivery apparatus of any one of Statements 1-9, wherein the first surface coating is highly reflective at wavelengths from about 700 nm to about 740 nm and highly transmissible at wavelengths of about 480 nm to about 550 nm.

Statement 11: The handheld laser delivery apparatus of any one of Statements 1-10, wherein the sub-nanosecond pulsed laser beam with the first wavelength at the first surface coating of the monolithic crystal has a fluence that does not exceed 1.5 $J/cm^2$ to prevent coating damage.

Statement 12: The handheld laser delivery apparatus of any one of Statements 1-11, wherein the second surface coating is highly reflective at wavelengths from about 480 nm to about 550 nm and highly transmissible at wavelengths from about 750 nm to about 850 nm.

Statement 13: The handheld laser delivery apparatus of Statement 12, wherein the second surface coating has a transmittance of greater than or equal to 75% at wavelengths from about 750 to about 850 nm.

Statement 14: The handheld laser delivery apparatus of Statement 12, wherein the second surface coating has a transmittance of 25% to 35% at wavelengths from about 730 nm to about 750 nm.

Statement 15: The handheld laser delivery apparatus of Statement 14, wherein the transmittance of the second surface coating monotonically increases by a slope of 2% per nanometer at wavelengths from about 730 nm to about 750 nm.

Statement 16: The handheld laser delivery apparatus of any one of Statements 1-15, wherein the monolithic crystal has a parallelism between of the first surface coating and the second surface coating of up to about 5 arc seconds.

Statement 17: The handheld laser delivery apparatus of any one of Statements 6-16, wherein the beam delivery optical system comprises one of a telescope optics, a lens array, a diffractive beam splitter, or combinations thereof.

Statement 18: The handheld laser delivery apparatus of Statement 17, wherein the sub-nanosecond pulsed laser beam at the second wavelength output from the beam delivery optical system comprises a single solid beam or a plurality of fractionated microbeams.

Statement 19: The handheld laser delivery apparatus of Statement 18, wherein the sub-nanosecond pulsed laser beam at the second wavelength output from the beam delivery optical system is a single solid beam and has a fluence of about 0.1 $J/cm^2$ up to about 10 $J/cm^2$.

Statement 20: The handheld laser delivery apparatus of Statement 18, wherein the sub-nanosecond pulsed laser beam at the second wavelength output from the beam delivery optical system is a plurality of fractionated microbeams and each microbeam has a fluence of up to about 50 $J/cm^2$.

Statement 21: A laser delivery system for treatment of skin pigmentation comprising a pump beam delivery system operable to deliver a sub-nanosecond pulsed laser beam having a first wavelength of about 480 nm to about 550 nm; and a handheld laser delivery apparatus of any one of the preceding Statements connected to the pump beam delivery system, wherein the handheld laser delivery apparatus is operable to receive the sub-nanosecond pulsed laser beam having the first wavelength from the pump beam delivery system and output the sub-nanosecond pulsed laser beam at a second wavelength of about 700 nm to about 740 nm.

Statement 22: The laser delivery system of Statement 21, wherein the second wavelength is about 730 nm.

Statement 23: The laser delivery system of Statement 21, wherein the first wavelength is about 532 nm.

Statement 24: The laser delivery system of Statement 21, wherein the pump beam delivery system comprises an articulated arm having a plurality of arms and a plurality of mirrors operable to direct the sub-nanosecond pulsed laser beam having a first wavelength to the inlet on the handheld laser delivery apparatus by rotation around at least one rotary joint connecting the plurality of arms.

Statement 25: The laser delivery system of Statement 24, wherein the plurality of mirrors are operable to preserve incident laser beam polarization.

Statement 26: The laser delivery system of one of Statements 21-25, wherein the sub-nanosecond pulsed laser beam having the first wavelength from the pump beam delivery system is circularly polarized.

Statement 27: The laser delivery system of any one of Statements 21-26, wherein the sub-nanosecond pulsed laser beam having the first wavelength has a pulse duration of about 20 ps to about 750 ps.

Statement 28: The laser delivery system of any one of Statements 21-27, wherein the sub-nanosecond pulsed laser beam having the second wavelength has a pulse duration of about 20 ps to about 750 ps.

Statement 29: A method of treating skin pigmentation in a patient in need thereof, wherein the method comprises delivering a sub-nanosecond pulsed laser beam having a second wavelength to the skin of the patient using the laser delivery system of any one of Statements 21-29.

Statement 30: A method of treating skin pigmentation in a patient in need thereof, wherein the method comprises generating, via a pump beam delivery system, a circularly polarized sub-nanosecond pulsed laser beam having a first wavelength of about 480 nm to about 550 nm; generating, via a handheld laser delivery apparatus, a sub-nanosecond pulsed laser beam having a second wavelength of about 700 nm to about 740 nm from the circularly polarized sub-nanosecond pulsed laser beam having the first wavelength; and delivering the sub-nanosecond pulsed laser beam having the second wavelength to the skin of the patient to target melanosomes while minimizing damage to vessels and surrounding tissue of the patient.

Statement 31: The method of Statement 30, wherein the first wavelength is about 532 nm and the second wavelength is about 730 nm.

Statement 32: The method of any one of Statements 30-31, wherein the sub-nanosecond pulsed laser beam having the second wavelength is linearly polarized.

What is claimed is:

1. A handheld laser delivery apparatus for treatment of skin pigmentation comprising:
   a sub-nanosecond pulsed laser beam having a first wavelength of 480 nm to 550 nm delivered from a pump beam delivery system; and
   a handheld body comprising:
      an inlet configured to receive the sub-nanosecond pulsed laser beam having the first wavelength; and
      an outlet configured to output the sub-nanosecond pulsed laser beam at a second wavelength and to deliver the sub-nanosecond pulsed laser beam at the second wavelength to the skin of a patient; and
   a Ti:Sapphire monolithic crystal mounted within the handheld body and configured to receive the sub-nanosecond pulsed laser beam at the first wavelength at a first end with a first surface coating and output the sub-nanosecond pulsed laser beam at the second wavelength of 700 nm to 740 nm at a second end with a second surface coating,
   wherein delivery of the sub-nanosecond pulsed laser beam at the second wavelength to the skin of the patient targets melanosomes for treatment of dermal and epidermal skin pigmentation comprising lentigines, freckles, seborrheic keratosis, melasma, and/or other skin pigmented lesions.

2. The handheld laser delivery apparatus of claim 1, wherein the first wavelength is 532 nm and the second wavelength is 730 nm.

3. The handheld laser delivery apparatus of claim 1, wherein the sub-nanosecond pulsed laser beam having the first wavelength and the sub-nanosecond pulsed laser beam having the second wavelength each have a pulse duration of 20 ps to 750 ps.

4. The handheld laser delivery apparatus of claim 1, further comprising:
   a quarter waveplate mounted on a rotary stage within the handheld body and operable to receive, from the inlet, the sub-nanosecond pulsed laser beam at the first wavelength as a circularly polarized beam and output the sub-nanosecond pulsed laser beam as a linearly polarized beam;
   a combination of a first homogenizer and a focus lens mounted within the handheld body and operable to receive the sub-nanosecond pulsed laser beam at the first wavelength from the quarter waveplate;
   a collimating lens mounted within the handheld body and operable to receive the sub-nanosecond pulsed laser beam at the second wavelength from the monolithic crystal;
   a second homogenizer mounted within the handheld body and operable to receive the sub-nanosecond pulsed laser beam from the collimating lens; and
   a beam delivery optical system mounted within the handheld body and operable to receive the sub-nanosecond pulsed laser beam from the second homogenizer and output the sub-nanosecond pulsed laser beam to the outlet of the handheld body.

5. The handheld laser delivery apparatus of claim 1, wherein the Ti:Sapphire monolithic crystal has a linear absorption for a double pass pumping configuration of greater than 90%, and has an internal absorption coefficient between 3.8 $cm^{-1}$ and 4.2 $cm^{-1}$ at the first wavelength.

6. The handheld laser delivery apparatus of claim 1, wherein the first surface coating has a reflectivity of at least 75% at wavelengths from 700 nm to 740 nm and a transmittance of at least 75% at wavelengths from 480 nm to 550 nm.

7. The handheld laser delivery apparatus of claim 1, wherein the sub-nanosecond pulsed laser beam with the first wavelength at the first surface coating of the monolithic crystal has a fluence that does not exceed 1.5 $J/cm^2$ to prevent coating damage.

8. The handheld laser delivery apparatus of claim 1, wherein the second surface coating has a reflectivity of at least 75% at wavelengths from 480 nm to 550 nm and a transm ittance of at least 75% at wavelengths from 750 nm to 850 nm.

9. The handheld laser delivery apparatus of claim 8, wherein the second surface coating has a transmittance of 25% to 35% at wavelengths from 730 nm to 750 nm.

10. The handheld laser delivery apparatus of claim 9, wherein the transmittance of the second surface coating monotonically increases by a slope of 2% per nanometer at wavelengths from 730 nm to 750 nm.

11. The handheld laser delivery apparatus of claim 1, wherein the monolithic crystal has a parallelism between of the first surface coating and the second surface coating of up to 5 arc seconds.

12. The handheld laser delivery apparatus of claim 1, wherein the sub-nanosecond pulsed laser beam having a second wavelength has a melanosome to blood absorption ratio of greater than 50.

13. The handheld laser delivery apparatus of claim 1, wherein delivery of the sub-nanosecond pulsed laser beam at the second wavelength to the skin of the patient minimizes adverse effects comprising erythema, hemorrhage, and/or damage to vessels and surrounding tissue of the patient.

14. A laser delivery system for treatment of skin pigmentation comprising:
    a pump beam delivery system configured to deliver a sub-nanosecond pulsed laser beam having a first wavelength of 480 nm to 550 nm; and
    a handheld laser delivery apparatus connected to the pump beam delivery system, wherein the handheld laser delivery apparatus is configured to:
        receive, at a first end of a Ti:Sapphire monolithic crystal with a first surface coating, the sub-nanosecond pulsed laser beam having the first wavelength from the pump beam delivery system;
        output, at a second end of the Ti:Sapphire monolithic crystal with a second surface coating, the sub-nanosecond pulsed laser beam at a second wavelength of 700 nm to 740 nm; and
        deliver the sub-nanosecond pulsed laser beam at the second wavelength to the skin of a patient,
    wherein delivery of the sub-nanosecond pulsed laser beam at the second wavelength to the skin of the patient targets melanosomes for treatment of dermal and epidermal skin pigmentation comprising lentigines, freckles, seborrheic keratosis, melasma, and/or other skin pigmented lesions.

15. The laser delivery system of claim 14, wherein the first wavelength is 532 nm and the second wavelength is 730 nm.

16. The laser delivery system of claim 14, wherein the pump beam delivery system comprises an articulated arm having a plurality of arms and a plurality of mirrors operable to direct the sub-nanosecond pulsed laser beam having a first wavelength to the inlet on the handheld laser delivery apparatus by rotation around at least one rotary joint connecting the plurality of arms.

17. The laser delivery system of claim 14, wherein the sub- nanosecond pulsed laser beam having the first wavelength and the sub-nanosecond pulsed laser beam having the second wavelength each have a pulse duration of 20 ps to 750 ps.

18. The laser delivery system of claim 14, wherein the sub-nanosecond pulsed laser beam having a second wavelength has a melanosome to blood absorption ratio of greater than 50.

19. The laser delivery system of claim 14, wherein delivery of the sub-nanosecond pulsed laser beam at the second wavelength to the skin of the patient minimizes adverse effects comprising erythema, hemorrhage, and/or damage to vessels and surrounding tissue of the patient.

20. A method of treating skin pigmentation in a patient in need thereof, wherein the method comprises:
    generating, via a pump beam delivery system, a circularly polarized sub-nanosecond pulsed laser beam having a first wavelength of 480 to 550 nm;
    generating, via a handheld laser delivery apparatus comprising a Ti:Sapphire monolithic crystal with a first surface coating at a first end and a second surface coating at a second end, a sub-nanosecond pulsed laser beam having a second wavelength of 700 nm to 740 nm from the circularly polarized sub-nanosecond pulsed laser beam having the first wavelength; and
    delivering the sub-nanosecond pulsed laser beam having the second wavelength to the skin of the patient to target melanosomes for treatment of dermal and epidermal skin pigmentation comprising lentigines, freckles, seborrheic keratosis, and/or melasma.

21. The method of claim 20, wherein the first wavelength is 532 nm and the second wavelength is 730 nm.

22. The method of claims 20, wherein the sub-nanosecond pulsed laser beam having the second wavelength is linearly polarized.

* * * * *